US006536430B1

(12) United States Patent
Smith (10) Patent No.: US 6,536,430 B1
(45) Date of Patent: Mar. 25, 2003

(54) PORTABLE ANESTHESIA REBREATHING SYSTEM

(76) Inventor: Charles A. Smith, 811 Starlite Dr., Louisville, KY (US) 40207

( * ) Notice: Subject to any disclaimer, the term of this patent is extended or adjusted under 35 U.S.C. 154(b) by 26 days.

(21) Appl. No.: 09/685,399

(22) Filed: Oct. 10, 2000

Related U.S. Application Data (63) Continuation-in-part of application No. 08/715,776, filed on Sep. 19, 1996, now abandoned.
(60) Provisional application No. 60/158,086, filed on Oct. 7, 1999.

(51) Int. Cl.⁷ ............................................. A61M 16/00
(52) U.S. Cl. ........................ 128/204.18; 128/204.15; 128/204.22; 128/203.28
(58) Field of Search ................... 128/204.15, 204.22, 128/203.14, 203.28, 20.28, 206.16

(56) References Cited

U.S. PATENT DOCUMENTS

| | | | | |
|---|---|---|---|---|
| 3,707,965 A | * | 1/1973 | Guzay | 128/205.28 |
| 4,150,670 A | * | 4/1979 | Jewett et al. | 128/204.22 |
| 4,188,946 A | * | 2/1980 | Watson et al. | 128/204.22 |
| 4,991,576 A | * | 2/1991 | Henkin et al. | 128/202.27 |
| 5,520,172 A | * | 5/1996 | Obermayer | 128/203.28 |
| 5,682,876 A | * | 11/1997 | Pernetti et al. | 128/202.27 |
| 5,769,072 A | * | 6/1998 | Olsson et al. | 128/204.22 |
| 5,806,513 A | * | 9/1998 | Tham et al. | 128/203.12 |
| 5,848,591 A | * | 12/1998 | Weismann | 128/203.12 |

* cited by examiner

Primary Examiner—Glenn K. Dawson
Assistant Examiner—Michael Mendoza (57) ABSTRACT

A portable anesthesia administering system which includes a compact, lightweight unit that does not require a source of electrical power to provide regulated pressurized anesthesia gas to a patient. The operating elements include a disposable carbon dioxide absorber, a charcoal scavenger absorber, an oxygen pressure sensor and alarm for detecting a drop in the oxygen pressure below a pre-selected level. The unit utilizes an anesthesia vaporizer and regulator, an airway pressure limiting valve and airway inlet and outlet control valves to provide a gaseous anesthesia agent in pre-selected amounts. Attached to the disposable carbon dioxide absorber is a manifold block which provides for a plurality of anesthesia regulating and control elements to facilitate the administration of the anesthesia. Connected to the manifold block is an external breathing bag for assisting in the breathing of the patient.

4 Claims, 7 Drawing Sheets

PORTABLE ANESTHESIA REBREATHING SYSTEM

CROSS REFERENCE TO RELATED APPLICATION

This application claims priority to U.S. Provisional Patent Application Serial No. 60/158,086 filed on Oct. 7, 1999 entitled Portable Anesthesia Rebreathing System which is a continuation in part of U.S. patent application Ser. No. 08/715,776 filed Sep. 19, 1996 (now abandoned) both by Charles A. Smith.

BACKGROUND OF THE INVENTION

This invention relates generally to a portable system for administering anesthetics to a patient at a location remote from the traditional hospital operating room. There has been a long felt need for a simple, reliable, effective portable anesthesia machine which could be easily operated at a site where health care or emergency services need be provided where the procedure is not complex but may necessarily require administration at a remote location. Typically, for example, dentists have found it necessary to have access to anesthetic services for such procedures as the extraction of wisdom teeth. Similarly, the need has arisen for anesthesia to be administered to victims of earthquakes, floods, hurricanes and the like under emergency conditions and in locations remote from an established health care facility. Also, the military recognizes the benefits of having a truly portable anesthesia rebreathing system. Also, there exists an economic incentive to develop such a system simply because more procedures may be performed in a doctor's office or on an out patient basis, thus reducing costly hospital charges.

Heretofore, however, anesthesia machines have required a source of electrical power as well as anesthesia gas and oxygen or air. Thus, the portability of such units has been significantly limited in the past. Also, the traditional anesthesia units have suffered from the prospect of cross-contaminating patients by virtue of the fact that the CO2 removal system has been made up of a large canister of soda lime used sequentially for patient after patient. Thus, in those environments where there is an epidemic, the use of anesthesia may contribute to the spread of infection. Cross contamination in the present system is eliminated because the unit uses a single, easily disposable, canister containing $CO_2$ absorbent. Moreover, the simplicity of the present invention allows for the easy cleaning and sterilization or disposal of any part that is contacted by the patient expired gas. The disposable $CO_2$ absorbent canister is the subject of U.S. Pat. No. 5,558,088 of Charles A. Smith, the inventor of the instant invention.

SUMMARY OF THE INVENTION

The present invention is directed to an improved anesthesia system which typically functions as a closed system and overcomes many of the shortcomings of the prior art systems. The present invention is a portable anesthesia administering system comprising tubes or conduits to and from a patient, operatively connected to a unit, which provides regulated, pressurized, anesthesia gas. The unit includes a frame having an upper and lower face and supporting structure therebetween defining a container space, said upper face containing a plurality of orifices each accepting an operating element of said unit therein with said elements projecting into the container space. One of said orifices receives a disposable carbon dioxide absorber supported by said upper face and is operably attached in flow communication with said conduits.

A second of said orifices receives and contains a charcoal absorber scavenging unit in flow communication with and downstream of an airway pressure limiting valve. A third of said orifices receives and contains an oxygen pressure gauge and regulator, said gauge/regulator being operably attached in flow communication with an in coming oxygen line. The unit also includes an alarm which is activated by a drop in oxygen pressure below a pre-selected level. A fourth one of said orifices receives and contains an oxygen flush control actuator which permits flushing of said system with oxygen from said oxygen line. A fifth of said orifices receives and contains an airway pressure gauge connected in flow communication with said system thereby providing continuous monitoring of the pressure within the system.

The system also includes an anesthesia vaporizer and regulator mounted on said lower plate and extending into said container space connected in flow communication with said conduits through a manifold block to provide a gaseous anesthesia agent such as Sevoflurane, produced by Abbott Laboratories, Inc. in pre-selected amounts from a self contained internal reservoir of said agent, said manifold block being supported by and in flow communication with said disposable carbon dioxide absorber and including a body having an interior gas containing space a portion of which functions as a mixing chamber.

The body has a plurality of conduits in flow communication with said space for channeling anesthesia gas to and from a patient and providing flow communication to a plurality of anesthesia regulating and control elements. One of such said conduits terminates in a port which permits flow communication with said airway pressure gauge. A second of said conduits terminates in a port permitting a flow communication with an external breathing bag for assisting the breathing of the patient. A third conduit terminates in a port permitting flow communication with an airway pressure limiting valve and a fourth conduit terminates in a port permitting flow communication with said oxygen pressure sensor. Fifth and sixth conduits are in flow communication with inlet and outlet flow control valves connected in line with said breathing tubes. Seventh and eighth conduits are in flow communication with inlet and outlet terminals of the carbon dioxide absorber. A sixth of said orifices receives and contains a fresh gas outlet connected to said anesthesia vaporizer and regulator which provides a source of anesthesia gas. In addition air is introduced through a fresh gas line to a fresh gas inlet port in said block so that both oxygen and air are available at all times if needed. The above combination of elements provides a self contained portable unit. Also advantageously the upper plate may contain an orifice for receiving and storing a second disposable carbon dioxide absorber positioned and adapted to receive the manifold block to provide continuous operation of the system and yet avoid cross contamination in the sequential treatment of patients.

It should be noted that the portable anesthesia unit of this invention is self contained and requires no electrical power source but only a single oxygen gas hose line and preferably a single air line, either one or both of which can be run from an independent tank or other source located a considerable distance away from the anesthesia unit itself. This feature gives a considerable advantage to the versatility and mobility of the unit since frequently it may be in a situation in metro disaster environments where it is not feasible to move large oxygen or air tanks into the immediate vicinity of patients requiring anesthesia.

DESCRIPTION OF THE PREFERRED EMBODIMENT

Figure 1:
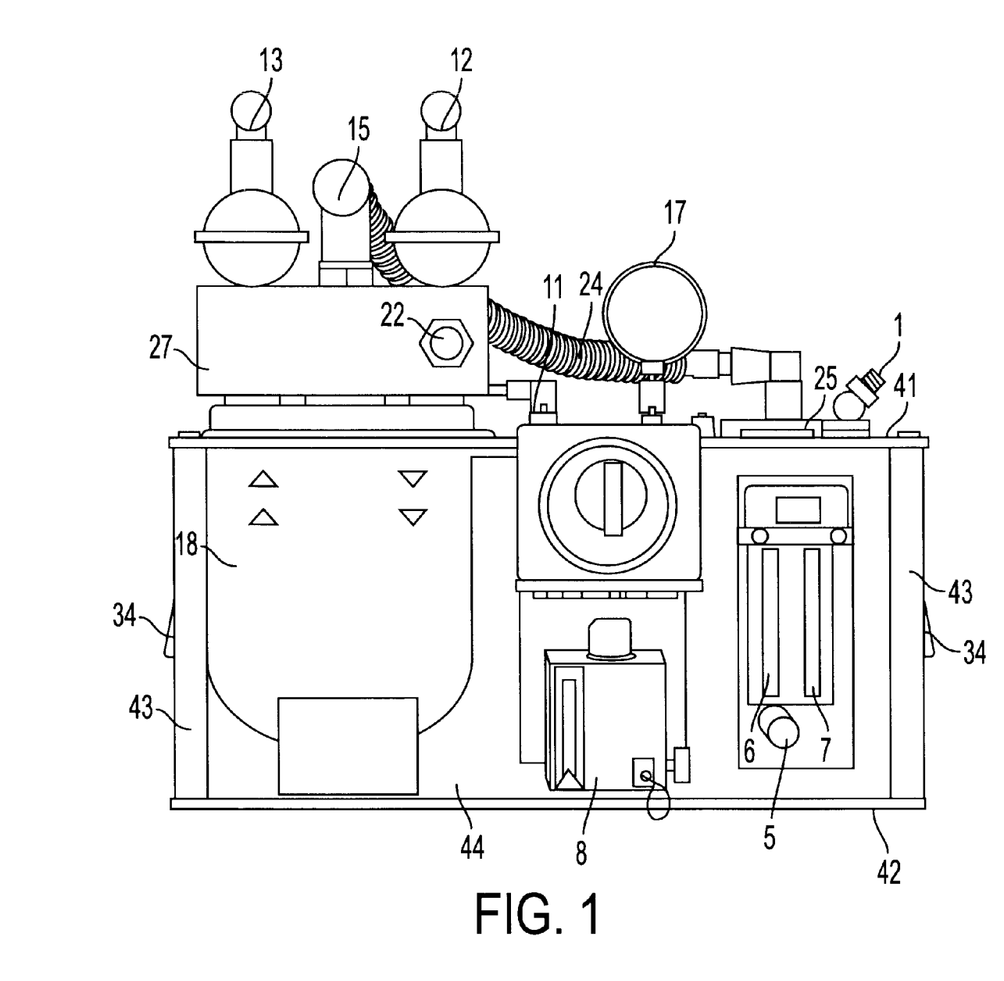
FIG. 1 is a front view of portable anesthesia system of this invention.

Referring to FIG. 1 the portable anesthesia administrating system is shown which includes upper and lower plates 41 and 42 respectively which are held in essentially parallel spaced relationship by supporting posts 43 defining a container space 44 there between. Upper plate 41 includes a number of orifices each of which accepts an operating element of the unit therein with the element then projecting into the container space. The following is an index identifying each operating element by number for ease of identification and location in the drawings.

Operating Elements

1. Oxygen Connector with Check Valve
2. Oxygen Supply Filter
3. Oxygen Supply Pressure Gauge, 0–100 psi
4. Low Oxygen Supply Pressure Alarm
5. Oxygen Flow Control Valve
6. Oxygen Flowmeter, Fine, 0–4 lpm
7. Oxygen Flowmeter, Coarse, 0–10 lpm
8. Vaporizer, Temperature Compensated
9. Check Valve between Vaporizer and Common Gas Outlet
10. Oxygen Flush Valve, 50 lpm
11. Common Gas Outlet, Key Index with Locking Device
12. Exhalation Valve with 22 mm Connector
13. Inhalation Value with 22 mm Connector
14. Oxygen Sensor
15. Adjustable Pressure Limiter (APL) Valve with 19 mm Connector
16. Instrumentation Ports, Key Index, Locking
17. Pressure Gauge, Breathing System, −40 to +80 cmH$_2$O
18. THERMH$_2$OSORB™CO$_2$ Absorber/Humidifier Canister
19. Foam, Absorbent Granule Barriers (Polyurethane)
20. Elbow for Breathing Bag
21. Breathing Bag
22. Bag Elbow Connection Port
23. Hose, Fresh Gas, Key Index and Locking on both Ends
24. Hose, Waste Gas Scavenging
25. Filter/Absorber for Waste Anesthesia Gas (Halogenated Agents)
26. Access Port for Breathing System Pressure Monitoring
27. Manifold Block, CO$_2$ Absorber System
28. Inhalation Valve Port
29. Exhalation Valve Port
30. Test Plug for Breathing Circuit Pressure Testing
31. Secondary (Spare) THERMH$_2$OSORB™CO$_2$ Canister with Seal Caps
32. Fresh Gas Connection to Manifold Block
33. Checkout Procedure Steps List
34. Lifting Handles
41. Upper Plate
42. Lower Plate
43. Supporting Posts
44. Container Space
46. Inhalation Conduits
47. Exhalation Conduits
51–56. Orifices In practice it can be seen that what is presented is a simple straightforward portable anesthesia administration system having application wherever anesthesia is required. The system can best be described by describing its function in actual use.

The first step is to connect a mask not shown and inhalation and exhalation conduits 46 and 47 respectively to inhalation and exhalation valves 13 and 12 respectively. The inhalation and exhalation conduits can be of the typical corrugated variety commonly in use in such medical applications. However, most preferably they are of the variety which are the subject of U.S. Pat. Nos. 5,377,670; 5,623,922 and 5,735,286 which patents are herein incorporated by reference.

Having thus connected the conduits, the next step is to flush the system with oxygen purging residual gasses therefrom. Activation of the oxygen flush valve 10 charges the patient breathing system with 100% oxygen. The oxygen is forced at 50 liters per minute through the fresh gas outlet II into the breathing bag 21 and then through the THERMH$_2$OSORB™ absorber/humidifier 18. The preferred absorber/humidifier for use in this invention is described and claimed in U.S. Pat. Nos. 5,143,060; 5,228,435; 5,360,002; and 5,558,088 all of which are incorporated herein by reference. It contains sufficient CO$_2$ absorbing material such as soda lime to accommodate a single patient and is referred to as a single patient use disposable carbon dioxide absorber.

The oxygen continues to flow through the open inspiratory valve 13 to the patient mask. The oxygen sensor 14 will signal 100% oxygen concentration to the oxygen monitor (optional). At this stage, all gasses from a previous exhalation present in the breathing circuit will be flushed out by the 100% oxygen gas flow and all carbon dioxide will be removed by the THERMH$_2$OSORB™ absorber/humidifier 18. The oxygen flush will have been completed at this stage.

The patient is then connected to the system. When the patient initiates an inhalation he creates a sub-atmospheric pressure in the system. This sub-atmospheric pressure opens the inspiratory or inhalation valve 13 while at- the same time the subatmospheric pressure keeps the expiratory or exhalation valve 12 closed. Since the fresh gas which is 100% oxygen will continue to flow from the fresh gas common gas outlet 11, excess gas will be evacuated from the breathing system through the adjustable pressure limiter valve 15. It should be noted that the common gas outlet has a key index with a locking device. This prevents tampering or unauthorized use of the anesthesia system by those not properly trained to do so. Similarly, it should be noted that the adjustable pressure limiter valve has a 19 mm connector while the exhalation and inhalation valves 12 and 13 have 22 mm connectors. This difference in size prevents any possibility of improperly connecting hoses in the system. Downstream of the pressure limiter valve 15 gas is removed through an active suction or charcoal filter scavenger system 25. The filter scavenger system contains an absorber for waste anesthesia gas which is preferably comprised of various halogenated agents.

As the patient begins to exhale, a positive pressure opens the exhalation or expiratory valve 12 but keeps the inhalation valve 13 closed. The patient exhales into the breathing bag 21 where the exhaled gas is mixed with fresh gas coming through manifold block 27 from fresh gas connection 32. The exhaled gas contains carbon dioxide and an anesthetic agent may be added from the vaporizer 48 to the completely dry 100% oxygen of the system.

As the exhalation continues the breathing bag 21 expands with a dry fresh gas mixture and with the exhaled patient gas containing $CO_2$. The extent of the expansion depends on the adjustment of the adjustable pressure limiter valve 15. Any excess fresh gas mixture from the manifold block is directed through the THERMH$_2$OSORB™ absorber/humidifier 18 to the adjustable pressure limiter valve 15 and from there the gas will be removed through an active suction or charcoal scavenger system 25 delivered through hose 24. The breathing bag is held in position and in fluid connection with the manifold block by virtue of the breathing bag elbow 20 inserted within the bag elbow connection port 22.

Assisted ventilation is initiated by squeezing the breathing bag 21. This creates a pressure which is registered on the patient system pressure gauge 17 which is calibrated to measure pressure between −40 to +80 centimeters of water. This is generally a sufficient operating range to meet the requirements of the patient. Upon exhalation the gas which contains $CO_2$ and the completely dry fresh gas mixture which may contain an anesthetic agent are transferred from the breathing bag 21 to the absorber/humidifier 18. The absorber removes the $CO_2$ from the exhaled gas. The foam granule barriers 19 prevent absorbent dust from entering the patient's breathing circuit as well as facilitate the humidifying of the gas before it is delivered to the patient.

Humidification occurs by virtue of water vapor from the patient's previous exhalation being condensed in the foam granule barriers and water vapor which is now reintroduced to the gas mixture as $CO_2$ is removed. Very typically the absorber is filled with soda lime which upon contact with $CO_2$ reacts to produce heat during the $CO_2$ removal process. The heat warms the gas now being returned to the patient. The inhalation and exhalation breathing conduits previously described can be insulated to preserve the heat so generated.

The gas once replenished with anesthetic agent and oxygen flows through the inhalation valve 13 to the patient in this closed system. The inspiratory oxygen concentration is recorded via the oxygen sensor 14. Advantageously, there is provided oxygen flow control valve 5 a fine and coarse oxygen flow meter 6 and 7. Typically the coarse flow meter permits adjustment between 0 and 10 liters per minute while the fine adjustment flow meter permits adjustment between 0 and 4 liters per minute. The pressure in the system as registered on the patient system pressure gauge 17 will depend on the adjustment of the adjustable pressure limiter valve and the patient's lung compliance. All excess gas will flow through the pressure limiter valve and will be removed through the scavenger charcoal system 25. At this stage the cycle may be repeated by once again applying pressure to the breathing bag 21.

Advantageously, there is provided a test plug 30 for breathing circuit pressure testing and a spare or secondary THERMH$_2$OSORB™ canister 31 which can be readied for use by simply removing the seal caps thereon and positioning manifold block 27 in flow communication therewith.

Also it is advantageous to provide lifting handles 34 to the structure between plates 41 and 42 to provide for the easy movement and placement of the anesthesia system of this invention.

Also, it should be noted that exhalation and inhalation valves 12 and 13 include a very dependable valve design for directional gas flow comprising a simple disk which is flat and retained on seating with a circular seat. This type valve is universally used in anesthesia machines for gas flow directional control. The valve opens with low pressure and low flow rates and depending on the weight of the disk creates negligible back pressure. The valve is virtually free of the possibility of reverse flow when in the closed position as long as complete contact is maintained between the disk and the total circumference of the seat. When used with low flows and pressure such as in anesthesia equipment, the valve operates quickly, precisely and dependably due to the low mass of the valve disk which reduces inertia of the disk to a minimum. The valve is normally in the closed position due to gravity acting on the disk when no flow is present. Valves of this type are limited to vertical flow positioning with flow pressure being applied to the bottom or top of the disk to open it. This disk is attached at one point on the circumference of the shell of the unit and tips up to allow gas flow.

Figure 2:
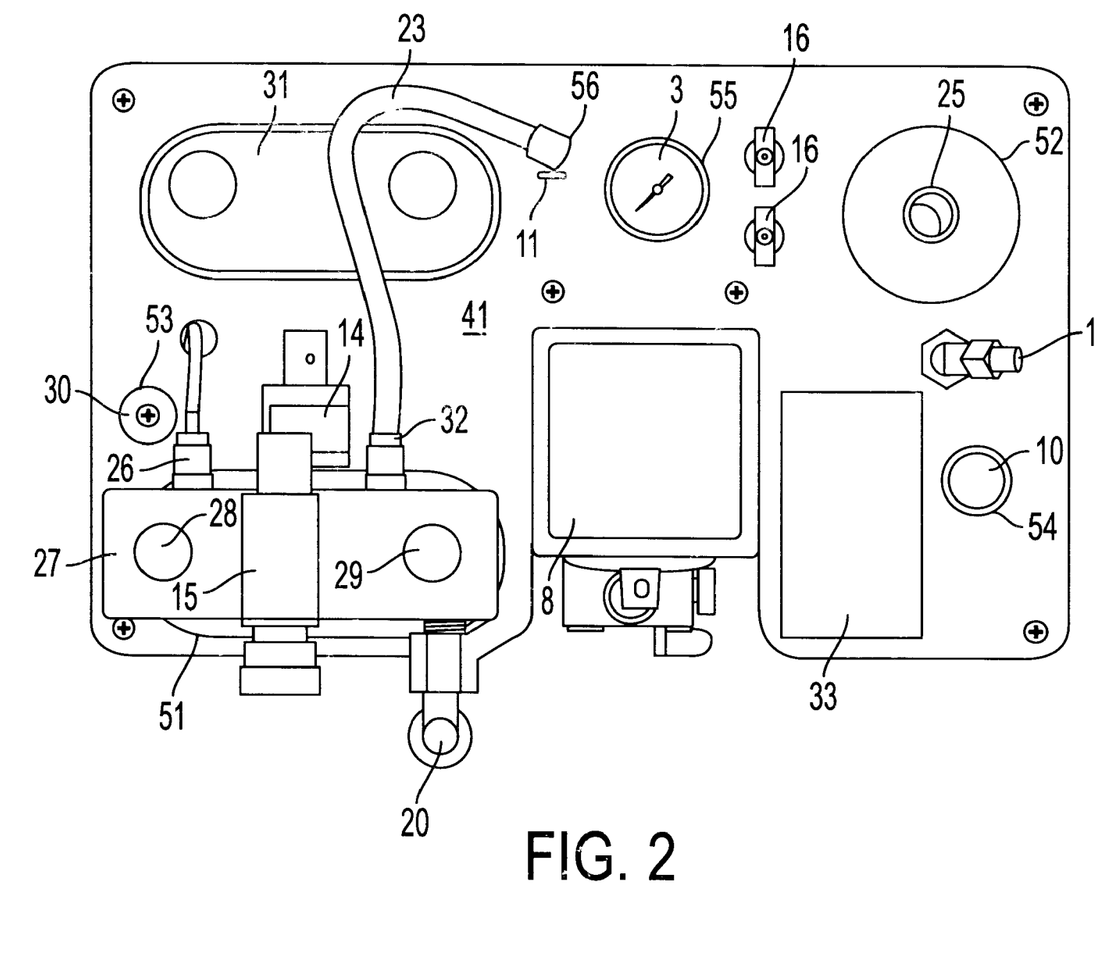
FIG. 2 is a top view of the portable anesthesia system showing the operating elements and their relationship to each other.
Figure 3:
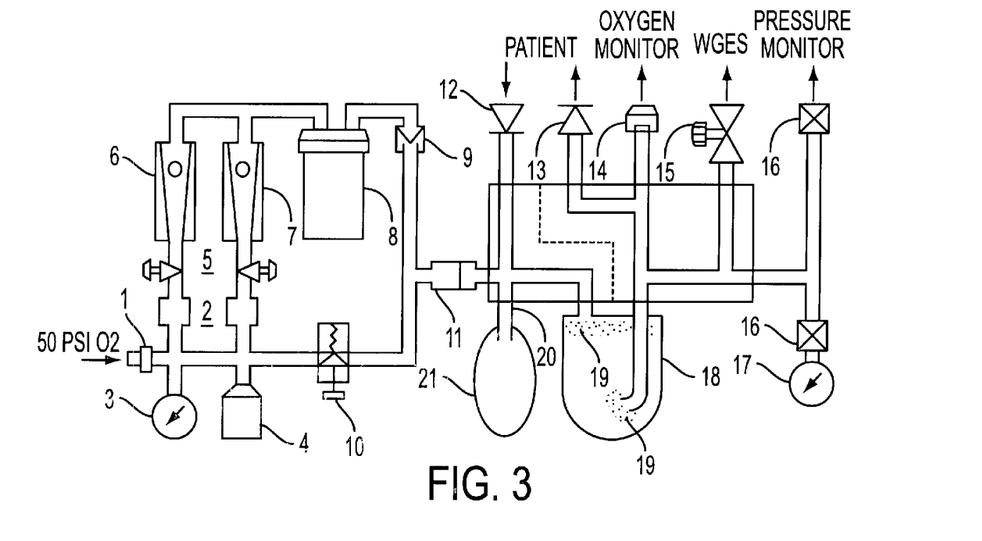
FIG. 3 is a schematic view of the anesthesia system of the invention.

As can be seen from FIG. 2 there are a plurality of orifices 51 though 56 in the upper plate 41 which receive and contain various of the operating elements. As best seen in FIG. 2, orifice 51 receives and contains the carbon dioxide absorber 18. Orifice 52 receives and contains the charcoal absorber 25. Orifice 53 receives and contains oxygen sensor 14. Orifice 54 receives and contains the oxygen flush control actuator and valve 10. Orifice 55 receives and contains an airway for oxygen pressure supply gauge 3 and lastly, orifice 56 receives and contains fresh or common gas outlet 11.

Figure 4:
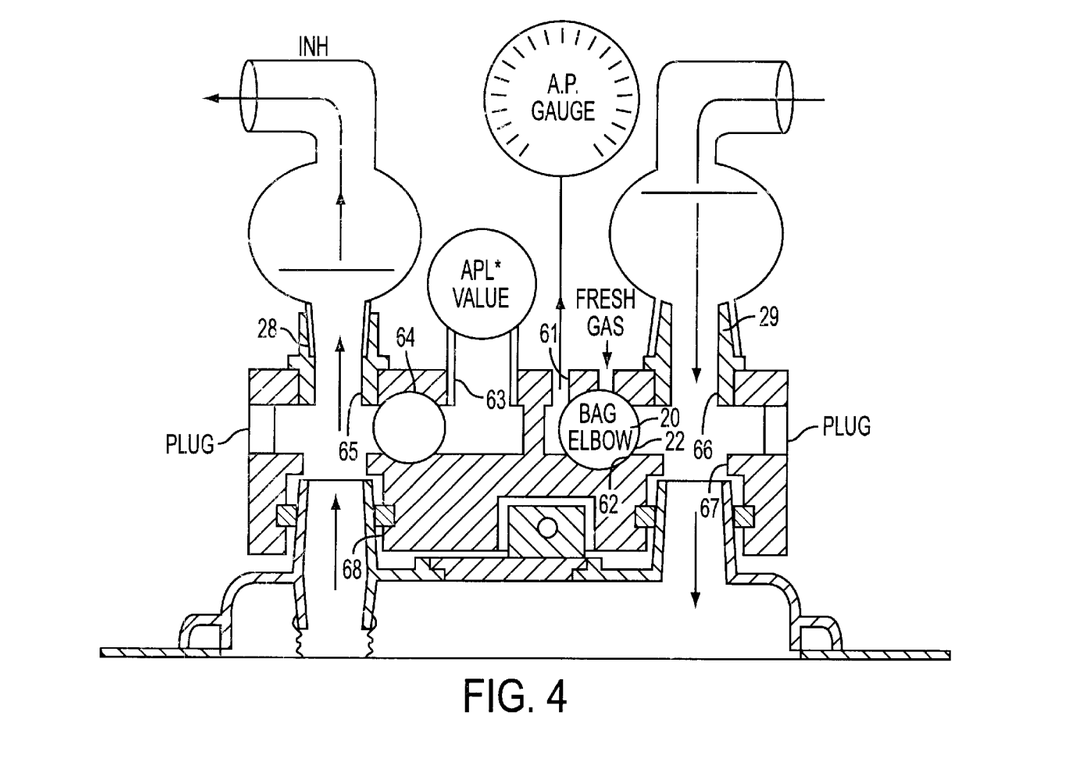
FIG. 4 is a front view of the manifold block of the invention in partial cross section showing its location atop the carbon dioxide absorbing canister.
Figure 5:
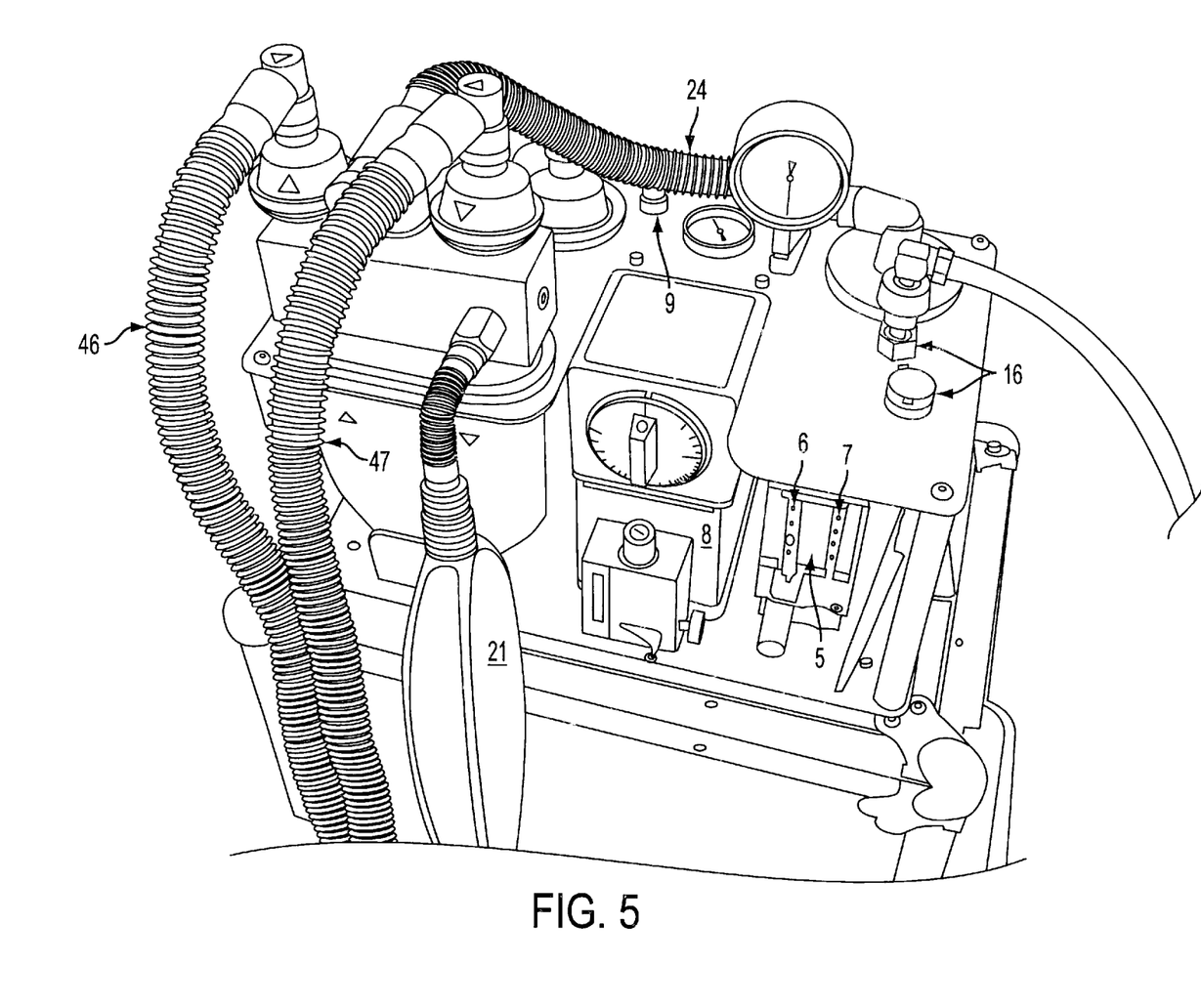
FIG. 5 is a perspective view of the anesthesia system of the present invention.
Figure 6:
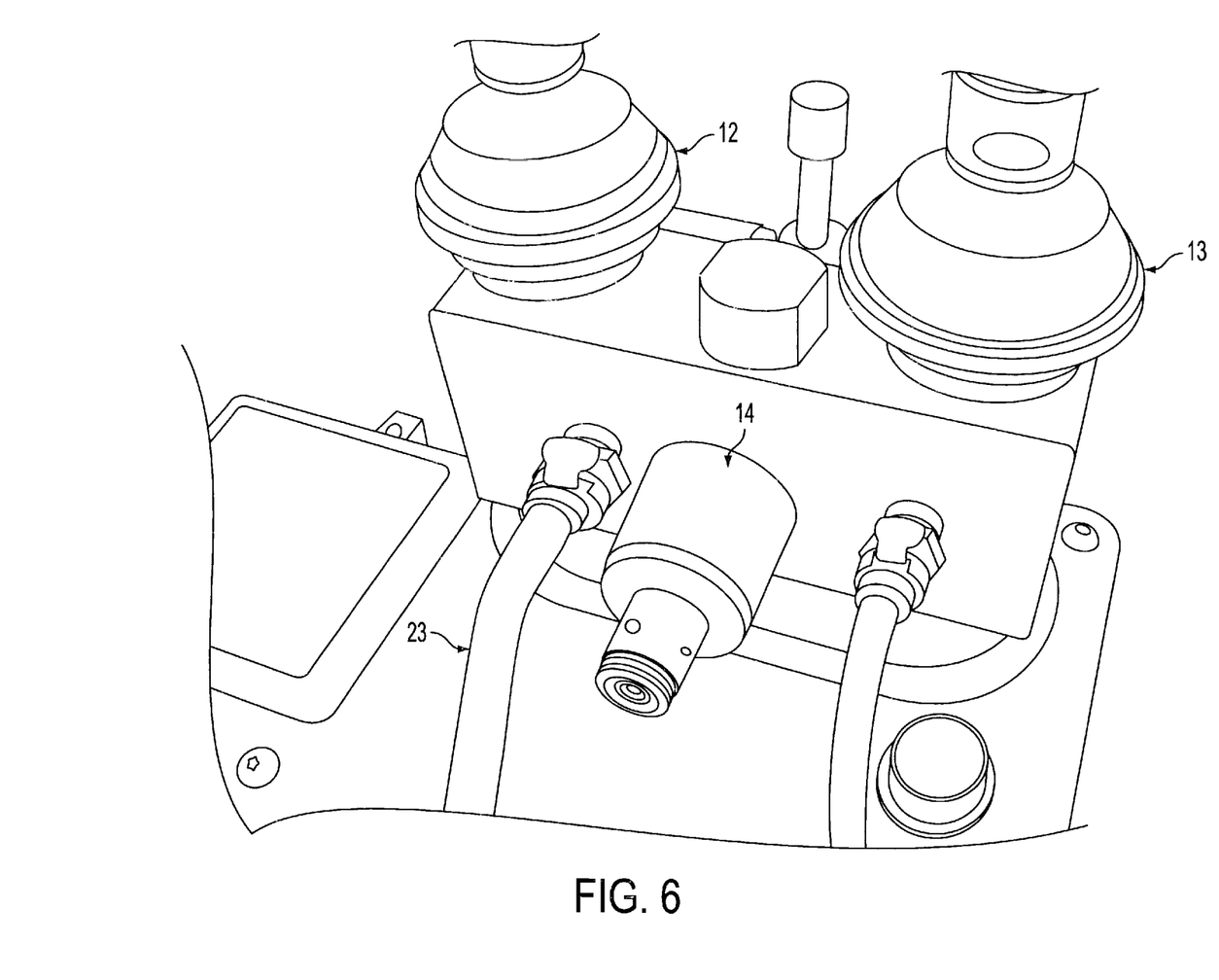
FIG. 6 is a perspective view of the manifold block of the present invention.

Lastly, with respect to the manifold block 27, it can be seen that there are a plurality of conduits which provide for the attachment of anesthesia regulating and control elements. These conduits are best seen in FIG. 4 designated by the numbers 61 through 68. Conduit 61 provides flow communication with the airway pressure gauge 3 while conduit 62 provides flow communication with breathing bag 21 through the elbow for the breathing bag 20 and the bag elbow connection port 22. Conduit 63 provides flow communication with the airway pressure limiting valve 15 while conduit 64 permits flow communication with the oxygen pressure sensor 3. Conduits 65 and 66 are in flow communication with inlet and outlet airway control valves 13 and 12. Lastly conduits 67 and 68 are in flow communication with the inlet and outlet terminals of the carbon dioxide absorber 18. As can be seen, the manifold block provides an important function in addition to that of a manifold by virtue of it serving in conjunction with the breathing bag at least in part as a mixing chamber. The manifold block is easily sterilizable upon removal of the appartences thereto. Except for the manifold block all of these elements are neatly positioned within the container space 44.

Figure 7:
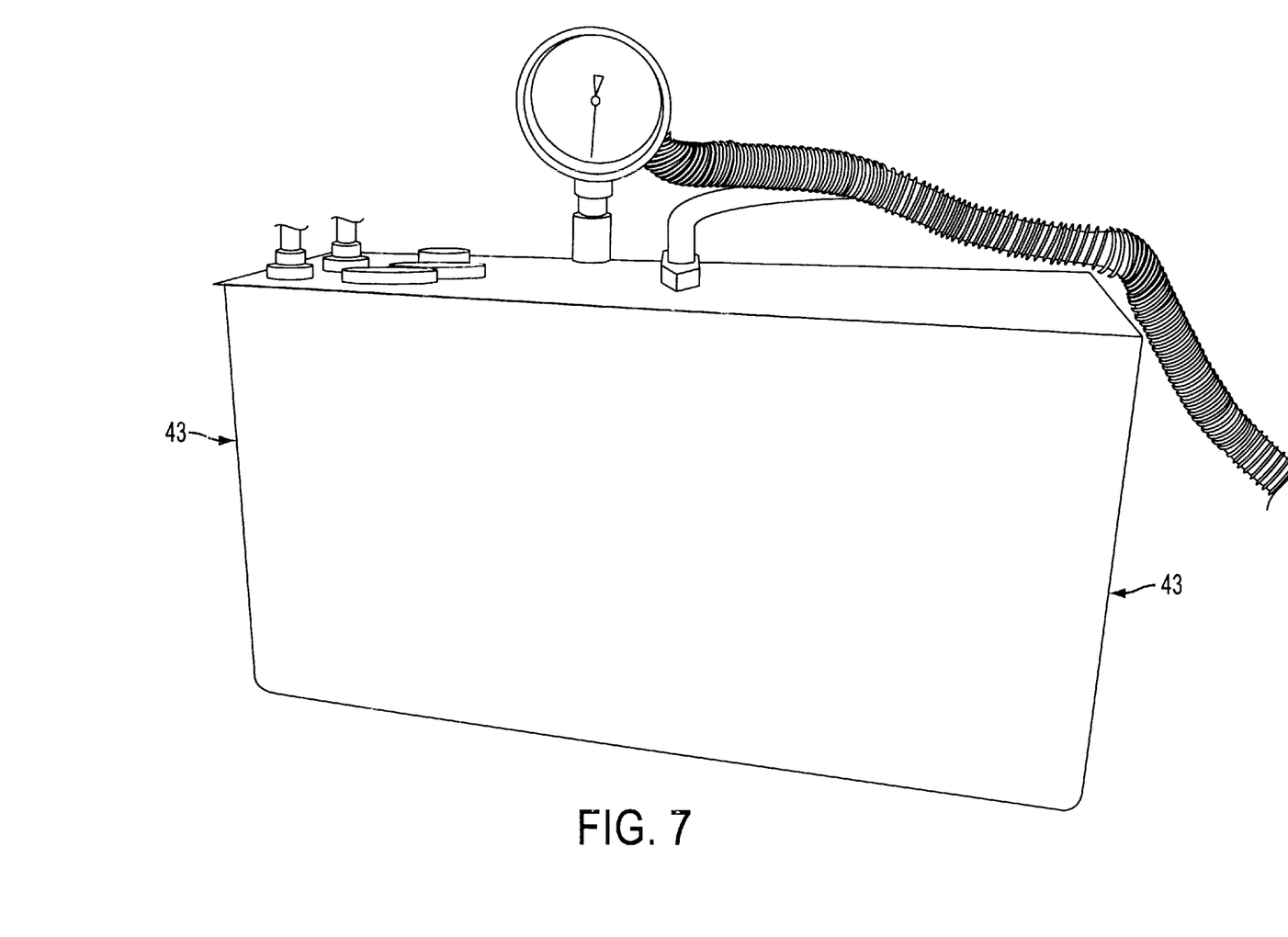
FIG. 7 is a back view of the anesthesia system of the present invention showing a fold down shelf.
Figure 8:
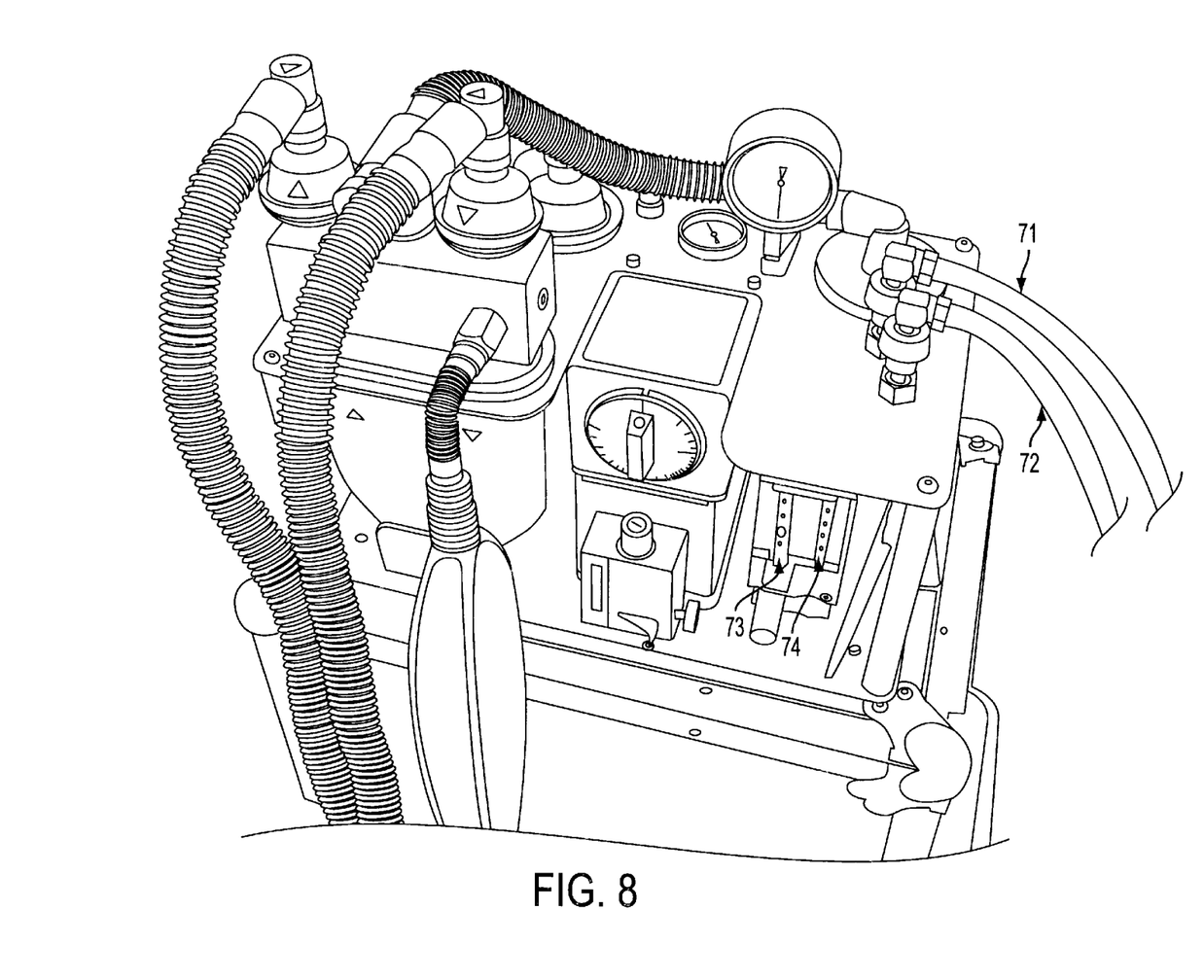
FIG. 8 is a perspective view showing the system when equipped to use both oxygen and air.

As can be seen and realized from the foregoing figures and description there are many advantageous features to the portable anesthesia system of this invention. For example, it is smaller than the typical $CO_2$ absorber system by at least 90% and significantly lighter perhaps as by as much as ten times lighter. The operating parts exposed to the patient's exhalant breath are totally cleanable or autoclavable. The unit can be located remotely from an anesthesia machine if it is used in conjunction therewith where the anesthesia machine would provide the breathing function in place of a breathing bag. Moreover, the design, size and weight promotes portable application for military and emergency rescue situations. The low cost directional valves provide for positive gas control and they are either cleanable or disposable. The absence of ferrous metal parts allows use in the vicinity of MRI procedures. The system is equipped with a positive locking means to hold the manifold block 27 to the $CO_2$ absorber in an aligned and indexed fashion. Also the connections to and from the manifold block incorporate size specific quick disconnect or tapered fit connections to eliminate leaks and O-rings used where applicable to insure a leak free system. No tools are thus required for preparation to clean, autoclave, set up or disassemble the unit. Also the reduced surface area of the compact unit makes it easier to clean and lower in cost than a typical anesthesia system. The unit accommodates any type circle or closed circuit breathing system and yet is easily integrated into those systems when advantageous to do so. Also it is evident that it is much quicker to change $CO_2$ absorbent canisters which can be stored for long periods of time since they are airtight. It is also possible to provide a fold-down shelf 70 shown in FIG. 7 attached to either upper plate 41 or support structure 43 for supporting various surgical or anesthesia items. FIG. 8 shows another embodiment of the invention which is preferred and which uses both oxygen and air as carrier gases for the anesthesia gas. Air and oxygen lines 71 and 72 respectively are shown entering the unit while flow meters 73 and 74 control their flow. FIG. 8 also shows a hose 75 for alternatively connecting the system of this invention to a commercial ventilator.

Having thus described the invention what is claimed is:

1. A portable anesthesia administering system comprising: breathing tubes to and from a patient operatively connected to a compact lightweight unit which provides regulated pressurized, anesthesia gas, said unit comprising a frame having an upper and lower face and supporting structure therebetween defining a container space, said upper face containing a plurality of orifices each accepting an operating element of said unit therein with said element projecting into the container space, one of said orifices receiving a disposable carbon dioxide absorber supported by said upper face and operably attached in flow communication with said breathing tubes, a second of said orifices receiving and containing a charcoal absorber scavenging unit in flow communication with and downstream of an airway pressure limiting valve, a third of said orifices receiving and containing an oxygen pressure gauge, said gauge being operably attached in flow communication with an incoming oxygen line, and having an alarm which is activated by a drop in oxygen pressure below a pre-selected level, a fourth of said orifices receiving and containing an oxygen flush control actuator which permits flushing of said system with oxygen from said oxygen line, a fifth of said orifices receiving and containing an airway pressure gauge connected in flow communication with said-system thereby providing continuous monitoring of the pressure within the system, and an anesthesia vaporizer and flow regulator mounted on said lower face and extending into said container space connected in flow communication with said breathing tubes through a manifold block to provide a gaseous anesthesia agent in pre-selected amounts from a self contained internal reservoir of said agent, said manifold block being supported by and in flow communication with said disposable carbon dioxide absorber and including a body having an interior gas containing space a portion of which functions as a mixing chamber, said body having a plurality of conduits in flow communication with said space for channeling anesthesia gas to and from a patient and providing flow communication to a plurality of anesthesia regulating and control elements one of such said conduits terminating in a port which permits flow communication with said airway pressure gauge, a second of said conduits terminating in a port permitting a flow communication with an external breathing bag for assisting the breathing of the patient, a third conduit terminating in a port permitting flow communication with an airway pressure limiting valve and a fourth conduit terminating in a port permitting flow communication with said oxygen sensor, fifth and sixth conduits in flow communication with inlet and outlet airway control valves connected in line with said breathing tubes, seventh and eighth conduits in flow communication with inlet and outlet terminals of said carbon dioxide absorber, a sixth of said orifices receiving and containing a fresh gas outlet connected to said anesthesia vaporizer and flow regulator as a source of anesthesia gas and through a fresh gas line to a fresh gas inlet port in said block providing a self contained portable unit.

2. The portable anesthesia administering system of claim 1 wherein said disposable carbon dioxide absorber contains soda lime as the carbon dioxide absorbing agent.

3. The portable anesthesia administering system of claim 2 wherein said disposable carbon dioxide absorber contains sufficient soda lime to accommodate a single patient.

4. The portable anesthesia administering system of claim 1 wherein said gaseous anesthesia agent is comprised of various halogenated agents.

* * * * *